United States Patent [19]

Müller-Hill et al.

[11] Patent Number: 5,218,100

[45] Date of Patent: Jun. 8, 1993

[54] DNA ENCODING FOR THE PRECURSOR PROTEIN OF APC POLYPEPTIDE ASSOCIATED WITH ALZHEIMER'S DISEASE

[75] Inventors: Benno Müller-Hill, Cologne; Jie Kang, Bonn; Hans-Georg Lemaire, Cologne, all of Fed. Rep. of Germany; Axel Unterbeck, West Haven, Conn.

[73] Assignee: Bayer Aktiengesellschaft, Leverkusen, Fed. Rep. of Germany

[21] Appl. No.: 144,297

[22] Filed: Jan. 15, 1988

[30] Foreign Application Priority Data

Jan. 30, 1987 [DE] Fed. Rep. of Germany ....... 3702789

[51] Int. Cl.$^5$ ............................................. C07H 21/02
[52] U.S. Cl. .................................... 536/23.5; 530/350; 530/388.1
[58] Field of Search ............................ 536/27, 28, 29

[56] References Cited

U.S. PATENT DOCUMENTS 4,666,829 5/1987 Glenner et al. .......................... 435/6

FOREIGN PATENT DOCUMENTS 0274826 7/1988 European Pat. Off.

OTHER PUBLICATIONS

Science, vol. 235, Feb. 1987, pp. 877–880; D. Goldgaber, et al., "Characterization and chromosomal localization of a cDNA encoding the cerebrovascular and the neuritic plaque amyloid peptides".
Proc. Natl. Acad. Sci. USA, vol. 83, Apr. 1986, pp. 2662–2666; A. Roher et al.: "Purification, ultrastructure, and chemical analysis of Alzheimer disease amyloid plaque core protein".
Proc. Natl. Acad. Sci. USA, vol. 82, Jun. 1985, pp. 4245–4249; C. L. Masters et al.: "Amyloid plaque core protein in Alzheimer disease and Down Syndrome".
Chemical Abstracts, vol. 104, 1986 p. 506, paragraph No. 127641f, Columbus, Ohio, US; C. L. Masters et al.: "Neuronal origin of a cerebral amyloid: neurofibrillary tangles of Alzheimer's disease contain the same protein as the amyloid of plaque cores and blood vessels", & EMBO J. 1985 4(11), 2757–2763.
Proc. Natl. Acad. Sci. USA, vol. 84, Jun. 1987, pp. 4190–4194; N. K. Robakis et al.: "Molecular cloning and characterization of a cDNA encoding the cerebrovascular and the neuritic plaque amyloid peptides".
Kang et al., "The Precursor of Alzheimer's Disease Amyloid A4 Protein Resembles a Cell-Surface Receptor," Nature, 325, 733–736 (1987).
Lemaire et al., "The Pre A $4_{695}$ Precursor Protein of Alzheimer's Disease A4 Amyloid is Encoded by 16 Exons," Nucleic Acids Research, 17(2), 517–522 (1989).
Vitek et al., "Absence of Mutation in the Beta-amyloid cDNA's Cloned From the Brains of Three Patients with Sporadic Alzheimer's Disease," Mol. Brain Res., 4, 121–131 (1988); Swiss Prot data base accession number is "B30320,".

Primary Examiner—Johnnie R. Brown
Assistant Examiner—L. Eric Crane
Attorney, Agent, or Firm—Sprung Horn Kramer & Woods

[57] ABSTRACT

The present invention relates to the precursor protein of amyloid plaque core (APC) polypeptide, to fragments of the precursor protein and to the diagnostic use of the precursor protein and of the fragments. Furthermore, the invention relates to the DNA coding for the precursor protein, to fragments of this DNA and to the diagnostic use of the DNA and of the fragments.

3 Claims, 3 Drawing Sheets

```
                                    AGTTTCCTCGGCAGCGGTAGGCGAGA  -121
GCACGCGGAGGAGCGTGCGCGGGGCCCCGGGAGACGGCGGCGGTGGCGGCGCGGGCAGAG   -61
CAAGGACGCGGCGGATCCCACTCGCACAGCAGCGCACTCGGTGCCCCGCGCAGGGTCGCG    -1
ATGCTGCCCGGTTTGGCACTGCTCCTGCTGGCCGCCTGGACGGCTCGGGCGCTGGAGGTA    60
 M  L  P  G  L  A  L  L  L  L  A  A  W  T  A  R  A  L  E  V
 1                 10                                      20
CCCACTGATGGTAATGCTGGCCTGCTGGCTGAACCCCAGATTGCCATGTTCTGTGGCAGA   120
 P  T  D  G  N  A  G  L  L  A  E  P  Q  I  A  M  F  C  G  R
                   30                                      40
CTGAACATGCACATGAATGTCCAGAATGGGAAGTGGGATTCAGATCCATCAGGGACCAAA   180
 L  N  M  H  M  N  V  Q  N  G  K  W  D  S  D  P  S  G  T  K
                         50                                60
ACCTGCATTGATACCAAGGAAGGCATCCTGCAGTATTGCCAAGAAGTCTACCCTGAACTG   240
 T  C  I  D  T  K  E  G  I  L  Q  Y  C  Q  E  V  Y  P  E  L
                         70                                80
CAGATCACCAATGTGGTAGAAGCCAACCAACCAGTGACCATCCAGAACTGGTGCAAGCGG   300
 Q  I  T  N  V  V  E  A  N  Q  P  V  T  I  Q  N  W  C  K  R
                         90                               100
GGCCGCAAGCAGTGCAAGACCCATCCCCACTTTGTGATTCCCTACCGCTGCTTAGTTGGT   360
 G  R  K  Q  C  K  T  H  P  H  F  V  I  P  Y  R  C  L  V  G
                        110                               120
GAGTTTGTAAGTGATGCCCTTCTCGTTCCTGACAAGTGCAAATTCTTACACCAGGAGAGG   420
 E  F  V  S  D  A  L  L  V  P  D  K  C  K  F  L  H  Q  E  R
                        130                               140
ATGGATGTTTGCGAAACTCATCTTCACTGGCACACCGTCGCCAAAGAGACATGCAGTGAG   480
 M  D  V  C  E  T  H  L  H  W  H  T  V  A  K  E  T  C  S  E
                        150                               160
AAGAGTACCAACTTGCATGACTACGGCATGTTGCTGCCCTGCGGAATTGACAAGTTCCGA   540
 K  S  T  N  L  H  D  Y  G  M  L  L  P  C  G  I  D  K  F  R
                        170                               180
GGGGTAGAGTTTGTGTGTTGCCCACTGGCTGAAGAAAGTGACAATGTGGATTCTGCTGAT   600
 G  V  E  F  V  C  C  P  L  A  E  E  S  D  N  V  D  S  A  D
                        190                               200
GCGGAGGAGGATGACTCGGATGTCTGGTGGGGCGGAGCAGACACAGACTATGCAGATGGG   660
 A  E  E  D  D  S  D  V  W  W  G  G  A  D  T  D  Y  A  D  G
                        210                               220
AGTGAAGACAAAGTAGTAGAAGTAGCAGAGGAGGAAGAAGTGGCTGAGGTGGAAGAAGAA   720
 S  E  D  K  V  V  E  V  A  E  E  E  V  A  E  V  E  E  E  E
                        230                               240
GAAGCCGATGATGACGAGGACGATGAGGATGGTGATGAGGTAGAGGAAGAGGCTGAGGAA   780
 E  A  D  D  D  E  D  D  E  D  G  D  E  V  E  E  E  A  E  E
                        250                               260
CCCTACGAAGAAGCCACAGAGAGAACCACCAGCATTGCCACCACCACCACCACCACCACA   840
 P  Y  E  E  A  T  E  R  T  T  S  I  A  T  T  T  T  T  T  T
                        270                               280
GAGTCTGTGGAAGAGGTGGTTCGAGTTCCTACAACAGCAGCCAGTACCCCTGATGCCGTT   900
 E  S  V  E  E  V  V  R  V  P  T  T  A  A  S  T  P  D  A  V
                        290                               300
GACAAGTATCTCGAGACACCTGGGGATGAGAATGAACATGCCCATTTCCAGAAAGCCAAA   960
 D  K  Y  L  E  T  P  G  D  E  N  E  H  A  H  F  Q  K  A  K
                        310                               320
```

FIG.1a

```
GAGAGGCTTGAGGCCAAGCACCGAGAGAGAATGTCCCAGGTCATGAGAGAATGGGAAGAG 1020
 E  R  L  E  A  K  H  R  E  R  M  S  Q  V  M  R  E  W  E  E
                   330                                    340

GCAGAACGTCAAGCAAAGAACTTGCCTAAAGCTGATAAGAAGGCAGTTATCCAGCATTTC 1080
 A  E  R  Q  A  K  N  L  P  K  A  D  K  K  A  V  I  Q  H  F
                   350                                    360

CAGGAGAAAGTGGAATCTTTGGAACAGGAAGCAGCCAACGAGAGACAGCAGCTGGTGGAG 1140
 Q  E  K  V  E  S  L  E  Q  E  A  A  N  E  R  Q  Q  L  V  E
                   370                                    380

ACACACATGGCCAGAGTGGAAGCCATGCTCAATGACCGCCGCCGCCTGGCCCTGGAGAAC 1200
 T  H  M  A  R  V  E  A  M  L  N  D  R  R  R  L  A  L  E  N
                   390                                    400

TACATCACCGCTCTGCAGGCTGTTCCTCCTCGGCCTCGTCACGTGTTCAATATGCTAAAG 1260
 Y  I  T  A  L  Q  A  V  P  P  R  P  R  H  V  F  N  M  L  K
                   410                                    420

AAGTATGTCCGCGCAGAACAGAAGGACAGACAGCACACCCTAAAGCATTTCGAGCATGTG 1320
 K  Y  V  R  A  E  Q  K  D  R  Q  H  T  L  K  H  F  E  H  V
                   430                                    440

CGCATGGTGGATCCCAAGAAAGCCGCTCAGATCCGGTCCCAGGTTATGACACACCTCCGT 1380
  R  M  V  D  P  K  K  A  A  Q  I  R  S  Q  V  M  T  H  L  R
                    450                                    460

GTGATTTATGAGCGCATGAATCAGTCTCTCTCCCTGCTCTACAACGTGCCTGCAGTGGCC 1440
 V  I  Y  E  R  M  N  Q  S  L  S  L  L  Y  N  V  P  A  V  A
                   470                                    480

GAGGAGATTCAGGATGAAGTTGATGAGCTGCTTCAGAAAGAGCAAAACTATTCAGATGAC 1500
 E  E  I  Q  D  E  V  D  E  L  L  Q  K  E  Q  N  Y  S  D  D
                   490                                    500

GTCTTGGCCAACATGATTAGTGAACCAAGGATCAGTTACGGAAACGATGCTCTCATGCCA 1560
 V  L  A  N  M  I  S  E  P  R  I  S  Y  G  N  D  A  L  M  P
                   510                                    520

TCTTTGACCGAAACGAAAACCACCGTGGAGCTCCTTCCCGTGAATGGAGAGTTCAGCCTG 1620
 S  L  T  E  T  K  T  T  V  E  L  L  P  V  N  G  E  F  S  L
                   530                                    540

GACGATCTCCAGCCGTGGCATTCTTTTGGGGCTGACTCTGTGCCAGCCAACACAGAAAAC 1680
 D  D  L  Q  P  W  H  S  F  G  A  D  S  V  P  A  N  T  E  N
                   550                                    560

GAAGTTGAGCCTGTTGATGCCCGCCCTGCTGCCGACCGAGGACTGACCACTCGACCAGGT 1740
 E  V  E  P  V  D  A  R  P  A  A  D  R  G  L  T  T  R  P  G
                   570                                    580
```

FIG. 1b

```
TCTGGGTTGACAAATATCAAGACGGAGGAGATCTCTGAAGTGAAGATGGATGCAGAATTC 1800
S  G  L  T  N  I  K  T  E  E  I  S  E  V  K  M  D  A  E  F
                        590                          600
CGACATGACTCAGGATATGAAGTTCATCATCAAAAATTGGTGTTCTTTGCAGAAGATGTG 1860
R  H  D  S  Q  Y  E  V  H  H  Q  K  L  V  F  F  A  E  D  V
                        610                          620
GGTTCAAACAAAGGTGCAATCATTGGACTCATGGTGGGCGGTGTTGTCATAGCGACAGTG 1920
G  S  N  K  G  A  I  I  G  L  M  V  G  G  V  V  I  A  T  V
                        630                          640
ATCGTCATCACCTTGGTGATGCTGAAGAAGAAACAGTACACATCCATTCATCATGGTGTG 1980
I  V  I  T  L  V  M  L  K  K  K  Q  Y  T  S  I  H  H  G  V
                        650                          660
GTGGAGGTTGACGCCGCTGTCACCCCAGAGGAGCGCCACCTGTCCAAGATGCAGCAGAAC 2040
V  E  V  D  A  A  V  T  P  E  E  R  H  L  S  K  M  Q  Q  N
                        670                          680
GGCTACGAAAATCCAACCTACAAGTTCTTTGAGCAGATGCAGAACTAGACCCCCGCCACA 2100
G  Y  E  N  P  T  Y  K  F  F  E  Q  M  Q  N  *
                        690
GCAGCCTCTGAAGTTGGACAGCAAAACCATTGCTTCACTACCCATCGGTGTCCATTTATA 2160
GAATAATGTGGGAAGAAACAAACCCGTTTTATGATTTACTCATTATCGCCTTTTGACAGC 2220
TGTGCTGTAACACAAGTAGATGCCTGAACTTGAATTAATCCACACATCAGTAATGTATTC 2280
TATCTCTCTTTACATTTTGGTCTCTATACTACATTATTAATGGGTTTTGTGTACTGTAAA 2340
GAATTTAGCTGTATCAAACTAGTGCATGAATAGATTCTCTCCTGATTATTTATCACATAG 2400
CCCCTTAGCCAGTTGTATATTATTCTTGTGGTTTGTGACCCAATTAAGTCCTACTTTACA 2460
TATGCTTTAAGAATCGATGGGGGATGCTTCATGTGAACGTGGGAGTTCAGCTGCTTCTCT 2520
TGCCTAAGTATTCCTTTCCTGATCACTATGCATTTTAAAGTTAAACATTTTTAAGTATTT 2580
CAGATGCTTTAGAGAGATTTTTTTTCCATGACTGCATTTTACTGTACAGATTGCTGCTTC 2640
TGCTATATTTGTGATATAGGAATTAAGAGGATACACACGTTTGTTTCTTCGTGCCTGTTT 2700
TATGTGCACACATTAGGCATTGAGACTTCAAGCTTTTCTTTTTTGTCCACGTATCTTTG 2760
GGTCTTTGATAAAGAAAAGAATCCCTGTTCATTGTAAGCACTTTTACGGGGCGGGTGGGG 2820
AGGGGTGCTCTGCTGGTCTTCAATTACCAAGAATTCTCCAAAACAATTTTCTGCAGGATG 2880
ATTGTACAGAATCATTGCTTATGACATGATCGCTTTCTACACTGTATTACATAAATAAAT 2940
TAAATAAAATAACCCCGGGCAAGACTTTTCTTTGAAGGATGACTACAGACATTAAATAAT 3000
CGAAGTAATTTTGGGTGGGGAGAAGAGGCAGATTCAATTTTCTTTAACCAGTCTGAAGTT 3060
TCATTTATGATACAAAAGAAGATGAAAATGGAAGTGGCAATATAAGGGGATGAGGAAGGC 3120
ATGCCTGGACAAACCCTTCTTTTAAGATGTGTCTTCAATTTGTATAAAATGGTGTTTTCA 3180
TGTAAATAAATACATTCTTGGAGGAGC-poly(A) tail
```

FIG.1c

DNA ENCODING FOR THE PRECURSOR PROTEIN OF APC POLYPEPTIDE ASSOCIATED WITH ALZHEIMER'S DISEASE

BACKGROUND OF THE INVENTION

1. Field of the Invention

The present invention relates to the precursor protein of amyloid plaque core (APC) polypeptide, to fragments of the precursor protein and to the diagnostic use of the precursor protein and of the fragments. Furthermore, the invention relates to the DNA coding for the precursor protein, to fragments of this DNA and to the diagnostic use of the DNA and of the fragments.

Alzheimer's disease was described as an independent clinical and pathological entity for the first time in the year 1907 by the German neurologist Alois Alzheimer (Alzheimer, A. (1907) Zentralblatt fur Nervenheilkunde und Psychiatrie, 177–179). It is the commonest degenerative brain disease of old people. In America alone about 2 million people are now suffering from the disease, and at least 100,000 die of it each year (Wurtman, R. J. (1985) Sci. Am. 252, 48–56).

The disease appears in people between 40 and 80 years of age. Those affected gradually lose their memory and their ability to concentrate. The state of mental deterioration advances until, within 3 to 10 years, the patients are unable either to speak, to think or to take care of themselves, and finally they die. The cause of this dementia is unknown. There is neither a definitive diagnosis nor a therapy.

Brain autopsies of people who have died of Alzheimer's disease reveal typical changes under the microscope as follows:

There has been a decrease in the number of neurons, especially in the parietal lobes, that is to say in the parts of the brain where the memory functions are localized. A loss of neurons which normally release acetylcholine is likewise clearly visible.

In addition, three extremely unusual structures appear in the cerebral cortex, these structures not existing in the brain of healthy people and thus being used for diagnosis (after death):

1) intracellular neurofibrils (NFTs, neurofibrillary tangles)

In the cytosome of neurons of the cerebral cortex and of the hippocampus are found bundles consisting of two filaments which are twisted around one another in the manner of a helix (PHFs, paired helical filaments).

2) extracellular amyloid plaques (APC, amyloid plaque core)

The neuritic plaques contain amyloid and the residues of dead cells, and they are scattered over the cerebral cortex, the hippocampus and the amygdaloid nucleus. The number of plaques is correlated with the degree of mental deterioration.

3) cerebrovascular amyloid (ACA, amyloid congophilic angiopathy)

Amyloid is the name given to a protein-rich composition. Such amorphous protein aggregates are to be found all around the blood vessels and in the wall of blood vessels in the brain.

The protein component of ACA has been isolated and sequenced (Glenner, G. G. & Wong, C. W. (1984) Biochem. Biophys. Res. Commun. 120, 885–890). The amino acid sequence has no homology with known protein sequences. The protein components of PHFs and APC have likewise been isolated and sequenced (Masters, C. L., Multhaupt, G., Simms, G., Pottgiesser, J., Martins R. N. and Beyreuther, K. (1985) EMBO 4, 2757–2763 and Masters, C. L., Simms, G., Weinman, N. A., Multhaupt, G., McDonald, B. L. and Beyreuther, K. (1985) Proc. Natl. Acad. Sci. USA 82, 4245–4249). The amino acid sequences indicate that all three polypeptides are probably the same one having a molecular weight of 4.5 kD. The relevant sequence is shown in boxes in FIGS. 1a–c (positions 597–638).

There are several hypotheses to explain the origin of this APC protein. It might be a normal protein in the brain (or even in another organ) in which either regulation of biosynthesis has become deranged or physiological breakdown is impaired. The accumulations of very large amounts might then be the cause of the disease. If it is an abnormal protein, and its unusual ability to aggregate causes the disease, it might also be coded for by a healthy human gene which was under faulty control due to some factor or other, for example, viruses, foodstuffs or environmental toxins. The fault might also comprise a modification of the original protein precursor. On the other hand however, a viral gene might also be responsible for synthesizing the APC protein.

In the work leading to the invention an attempt has now been made to establish the origin and nature of the APC protein, whose aggregation in the cerebral cortex is one of the main biochemical signs in Alzheimer patients, in order thereby to obtain a tool for improved diagnosis of Alzheimer's disease.

For this purpose, a human fetal brain c-DNA bank with pA+mRNA of the cerebral cortex was constructed.

The c-DNA was synthesized by the method of Okayama and Berg (Okayama, H. and Berg, P. Mol. Cell. Biol. 2, 161–170 (1982); Okayama, H. and Berg, P. Mol. Cell. Biol. 3, 280–289 (1983)), and the c-DNA was transformed into E. coli HB 101 (Aviv, H. and Leder, P. Proc. Natl. Acad. Sci. USA 69, 1408 (1972)). Each of the c-DNA banks obtained in this way contains more than $1 \times 10^6$ independent c-DNA clones.

To screen the bank, use was made of a DNA probe whose sequence was derived from the sequence of APC polypeptide. The chosen sequence corresponds to the amino acids in positions 10–16 of APC. The relevant sequence is indicated by a brace in FIG. 1c (positions 1815–1835). In order to ensure optimum hybridization, the degeneracy of the genetic code was taken into account, and a mixture having the following sequence

was prepared and used as probe. This is a 64-fold degenerate 20-mer. A test on 100,000 c-DNA clones from the human fetal cerebral cortex bank resulted in the isolation of a complete (full-length) c-DNA clone, having the serial No. EC 9.110, which codes for a protein which contains the APC sequence and thus represents the precursor protein of APC peptide. The sequence of the c-DNA, and the amino acid sequence of the coded protein, are to be found in FIG. 1. Sequence analysis was carried out by the dideoxy method (Sanger, F., Nicklen, S. and Coulson, A. R. Proc. Natl. Acad. Sci. USA 74, 5463–5467 (1977) and Guidelines for quick and simple Plasmid Sequencing, Handbook, (1986) Boehringer Mannheim GmbH, Biochemica, D-6800 Mannheim). Nothing is known at present about the natural function of the APC precursor protein.

SUMMARY OF THE INVENTION

Thus the present invention relates to the deoxyribonucleic acid of the sequence shown in FIG. 1 and to its functional equivalents. In this context, the term functional equivalents means that, owing to the degeneracy of the genetic code, individual nucleotides in the sequence can be exchanged or derivatized without this having an effect on the function of the nucleic acid. In particular, the invention relates to the DNA of the sequence shown in FIG. 1 from position 1 to position 2089, and to its functional equivalents. This part of the DNA is the part which codes for the precursor protein. Due to some peculiarities in the sequence, the protein and the corresponding DNA sequence are an interesting tool for the diagnosis of Alzheimer's disease at the molecular level. In this connection, the region from approximately position 600 to approximately position 900 is particularly worthy of mention. This part codes for a number of acidic amino acids which is unusually large in relation to the length of this section. Also worthy of very particular note are the seven consecutive threonines (position: DNA 819-840/amino acids 274-280). Such regions are particularly interesting for the development of DNA probes for diagnosis because, due to their unusual sequence, they are unique and thus allow highly specific detection.

The invention also relates to fragments of the DNA from FIG. 1 and to oligonucleotides derived from this DNA, and to their use as probes in diagnosis. The DNA is not used in its full length for hybridization experiments. Normally, fragments of a length of about 10 to 50 nucleotides are used for hybridizations. Longer fragments usually give rise to manipulation problems. Fragments with fewer than 10 nucleotides usually do not have adequate specificity, or the binding is too weak.

DETAILED DESCRIPTION OF THE INVENTION

The DNA shown in FIG. 1, and the fragments of this DNA, can be used very satisfactorily for the diagnosis of Alzheimer's disease, to detect mutations such as, for example, deletions, insertions and point mutations or rearrangement errors.

The present invention makes it possible to diagnose Alzheimer's disease on the molecular level. This applies equally to the presymptomatic diagnosis of Alzheimer's disease. The analyses can be carried out with known techniques of DNA technology, such as, for example, the techniques described by Antonarkais et al. (1985) in Hum. Gen 69, 1-14.

The present invention also includes the precursor protein coded for by the DNA, and the fragments of this protein. The detection of this protein or of the fragments likewise represents an approach to the diagnosis of Alzheimer's disease. Once again, the peculiarities of the sequence (amino acids: about position 200 to about position 290) are of particular importance. Fragments of the precursor protein, especially from the region 200 to 290, can be used very satisfactorily as antigens peptides for the preparation of polyclonal or monoclonal antibodies which, in turn, are used in diagnosis.

Functional equivalents in the context of the protein or the peptides means that variations, in the form of exchange of amino acids or derivatizations which have no effect on the function of these peptides, for example as antigens, are possible both in the sequence of the protein and in the peptides too.

Key to FIGS. 1 a–c.

Nucleotide sequence 5'→3' of the c-DNA clone which codes for the precursor protein of APC polypeptide, and the amino acid sequence derived from the DNA. The amino acids are designated using the following one-letter code:

| Amino acids | | |
|---|---|---|
| A | Ala | Alanine |
| B | Asx | AsN or Asp |
| C | Cys | Cysteine (cystine) |
| D | Asp | Aspartic acid |
| E | Glu | Glutamic acid |
| F | Phe | Phenylalanine |
| G | Gly | Glycerine |
| H | His | Histidine |
|   | HS | Homoserine |
|   | HSL | Homoserine lactone |
| I | Ile | Isoleucine |
| K | Lys | Lysine |
| L | Leu | Leucine |
| M | Met | Methionine |
| N | AsN | Asparagine |
|   | Nle | Norleucine |
| P | Pro | Proline |
| Q | Gln | Glutamine |
| R | Arg | Arginine |
| S | Ser | Serine |
| T | Thr | Threonine |
| V | Val | Valine |
| W | TrP | Tryptophan |
| Y | Tyr | Tyrosine |
| Z | Glx | Glu or GlN |
| X | not identified | |

It will be appreciated that the instant specification and claims are set forth by way of illustration and not limitation, and that various modifications and changes may be made without departing from the spirit and scope of the present invention.

What is claimed is:

1. A deoxyribonucleic acid of the sequence:

```
AGTTTCCTCGGCAGCGGTAGGCGAGA                       −121

GCACGCGGAGGAGCGTGCGCGGGGCCCCGG                   −91

GAGACGGCGGCGGTGGCGGCGCGGGCAGAG                   −61

CAAGGACGCGGCGGATCCCACTCGCACAGC                   −31

AGCGCACTCGGTGCCCCGCGCAGGGTCGCG                   −1

ATGCTGCCCGGTTTGGCACTGCTCCTGCTG                   30
 M  L  P  G  L  A  L  L  L  L

GCCGCCTGGACGGCTCGGGCGCTGGAGGTA                   60
 A  A  W  T  A  R  A  L  E  V

CCCACTGATGGTAATGCTGGCCTGCTGGCT                   90
 P  T  D  G  N  A  G  L  L  A

GAACCCCAGATTGCCATGTTCTGTGGCAGA                   120
 E  P  Q  I  A  M  F  C  G  R

CTGAACATGCACATGAATGTCCAGAATGGG                   150
 L  N  M  H  M  N  V  Q  N  G

AAGTGGGATTCAGATCCATCAGGGACCAAA                   180
 K  W  D  S  D  P  S  G  T  K

ACCTGCATTGATACCAAGGAAGGCATCCTG                   210
 T  C  I  D  T  K  E  G  I  L
```

-continued

```
CAGTATTGCCAAGAAGTCTACCCTGAACTG      240
 Q  Y  C  Q  E  V  Y  P  E  L

CAGATCACCAATGTGGTAGAAGCCAACCAA      270
 Q  I  T  N  V  V  E  A  N  Q

CCAGTGACCATCCAGAACTGGTGCAAGCGG      300
 P  V  T  I  Q  N  W  C  K  R

GGCCGCAAGCAGTGCAAGACCCATCCCCAC      330
 G  R  K  Q  C  K  T  H  P  H

TTTGTGATTCCCTACCGCTGCTTAGTTGGT      360
 F  V  I  P  Y  R  C  L  V  G

GAGTTTGTAAGTGATGCCCTTCTCGTTCCT      390
 E  F  V  S  D  A  L  L  V  P

GACAAGTGCAAATTCTTACACCAGGAGAGG      420
 D  K  C  K  F  L  H  Q  E  R

ATGGATGTTTGCGAAACTCATCTTCACTGG      450
 M  D  V  C  E  T  H  L  H  W

CACACCGTCGCCAAAGAGACATGCAGTGAG      480
 H  T  V  A  K  E  T  C  S  E

AAGAGTACCAACTTGCATGACTACGGCATG      510
 K  S  T  N  L  H  D  Y  G  M

TTGCTGCCCTGCGGAATTGACAAGTTCCGA      540
 L  L  P  C  G  I  D  K  F  R

GGGGTAGAGTTTGTGTGTTGCCCACTGGCT      570
 G  V  E  F  V  C  C  P  L  A

GAAGAAAGTGACAATGTGGATTCTGCTGAT      600
 E  E  S  D  N  V  D  S  A  D

GCGGAGGAGGATGACTCGGATGTCTGGTGG      630
 A  E  E  D  D  S  D  V  W  W

GGCGGAGCAGACACAGACTATGCAGATGGG      660
 G  G  A  D  T  D  Y  A  D  G

AGTGAAGACAAAGTAGTAGAAGTAGCAGAG      690
 S  E  D  K  V  V  E  V  A  E

GAGGAAGAAGTGGCTGAGGTGGAAGAAGAA      720
 E  E  E  V  A  E  V  E  E  E

GAAGCCGATGATGACGAGGACGATGAGGAT      750
 E  A  D  D  D  E  D  D  E  D

GGTGATGAGGTAGAGGAAGAGGCTGAGGAA      780
 G  D  E  V  E  E  E  A  E  E

CCCTACGAAGAAGCCACAGAGAGAACCACC      810
 P  Y  E  E  A  T  E  R  T  T

AGCATTGCCACCACCACCACCACCACCACA      840
 S  I  A  T  T  T  T  T  T  T

GAGTCTGTGGAAGAGGTGGTTCGAGTTCCT      870
 E  S  V  E  E  V  V  R  V  P

ACAACAGCAGCCAGTACCCCTGATGCCGTT      900
 T  T  A  A  S  T  P  D  A  V

GACAAGTATCTCGAGACACCTGGGGATGAG      930
 D  K  Y  L  E  T  P  G  D  E

AATGAACATGCCCATTTCCAGAAAGCCAAA      960
 N  E  H  A  H  F  Q  K  A  K

GAGAGGCTTGAGGCCAAGCACCGAGAGAGA      990
 E  R  L  E  A  K  H  R  E  R

ATGTCCCAGGTCATGAGAGAATGGGAAGAG     1020
 M  S  Q  V  M  R  E  W  E  E

GCAGAACGTCAAGCAAAGAACTTGCCTAAA     1050
 A  E  R  Q  A  K  N  L  P  K
```

-continued

```
GCTGATAAGAAGGCAGTTATCCAGCATTTC     1080
 A  D  K  K  A  V  I  Q  H  F

CAGGAGAAAGTGGAATCTTTGGAACAGGAA     1110
 Q  E  K  V  E  S  L  E  Q  E

GCAGCCAACGAGAGACAGCAGCTGGTGGAG     1140
 A  A  N  E  R  Q  Q  L  V  E

ACACACATGGCCAGAGTGGAAGCCATGCTC     1170
 T  H  M  A  R  V  E  A  M  L

AATGACCGCCGCCGCCTGGCCCTGGAGAAC     1200
 N  D  R  R  R  L  A  L  E  N

TACATCACCGCTCTGCAGGCTGTTCCTCCT     1230
 Y  I  T  A  L  Q  A  V  P  P

CGGCCTCGTCACGTGTTCAATATGCTAAAG     1260
 R  P  R  H  V  F  N  M  L  K

AAGTATGTCCGCGCAGAACAGAAGGACAGA     1290
 K  Y  V  R  A  E  Q  K  D  R

CAGCACACCCTAAAGCATTTCGAGCATGTG     1320
 Q  H  T  L  K  H  F  E  H  V

CGCATGGTGGATCCCAAGAAAGCCGCTCAG     1350
 R  M  V  D  P  K  K  A  A  Q

ATCCGGTCCCAGGTTATGACACACCTCCGT     1380
 I  R  S  Q  V  M  T  H  L  R

GTGATTTATGAGCGCATGAATCAGTCTCTC     1410
 V  I  Y  E  R  M  N  Q  S  L

TCCCTGCTCTACAACGTGCCTGCAGTGGCC     1440
 S  L  L  Y  N  V  P  A  V  A

GAGGAGATTCAGGATGAAGTTGATGAGCTG     1470
 E  E  I  Q  D  E  V  D  E  L

CTTCAGAAAGAGCAAAACTATTCAGATGAC     1500
 L  Q  K  E  Q  N  Y  S  D  D

GTCTTGGCCAACATGATTAGTGAACCAAGG     1530
 V  L  A  N  M  I  S  E  P  R

ATCAGTTACGGAAACGATGCTCTCATGCCA     1560
 I  S  Y  G  N  D  A  L  M  P

TCTTTGACCGAAACGAAAACCACCGTGGAG     1590
 S  L  T  E  T  K  T  T  V  E

CTCCTTCCCGTGAATGGAGAGTTCAGCCTG     1620
 L  L  P  V  N  G  E  F  S  L

GACGATCTCCAGCCGTGGCATTCTTTTGGG     1650
 D  D  L  Q  P  W  H  S  F  G

GCTGACTCTGTGCCAGCCAACACAGAAAAC     1680
 A  D  S  V  P  A  N  T  E  N

GAAGTTGAGCCTGTTGATGCCCGCCCTGCT     1710
 E  V  E  P  V  D  A  R  P  A

GCCGACCGAGGACTGACCACTCGACCAGGT     1740
 A  D  R  G  L  T  T  R  P  G

TCTGGGTTGACAAATATCAAGACGGAGGAG     1770
 S  G  L  T  N  I  K  T  E  E

ATCTCTGAAGTGAAGATGGATGCAGAATTC     1800
 I  S  E  V  K  M  D  A  E  F

CGACATGACTCAGGATATGAAGTTCATCAT     1830
 R  H  D  S  G  Y  E  V  H  H

CAAAAATTGGTGTTCTTTGCAGAAGATGTG     1860
 Q  K  L  V  F  F  A  E  D  V
```

-continued

```
GGTTCAAACAAAGGTGCAATCATTGGACTC    1890
 G  S  N  K  G  A  I  I  G  L

ATGGTGGGCGGTGTTGTCATAGCGACAGTG    1920
 M  V  G  G  V  V  I  A  T  V

ATCGTCATCACCTTGGTGATGCTGAAGAAG    1950
 I  V  I  T  L  V  M  L  K  K

AAACAGTACACATCCATTCATCATGGTGTG    1980
 K  Q  Y  T  S  I  H  H  G  V

GTGGAGGTTGACGCCGCTGTCACCCCAGAG    2010
 V  E  V  D  A  A  V  T  P  E

GAGCGCCACCTGTCCAAGATGCAGCAGAAC    2040
 E  R  H  L  S  K  M  Q  Q  N

GGCTACGAAAATCCAACCTACAAGTTCTTT    2070
 G  Y  E  N  P  T  Y  K  F  F

GAGCAGATGCAGAACTAGACCCCCGCCACA    2100
 E  Q  M  Q  N  *

GCAGCCTCTGAAGTTGGACAGCAAAACCAT    2130
TGCTTCACTACCCATCGGTGTCCATTTATA    2160
GAATAATGTGGGAAGAAACAAACCCGTTTT    2190
ATGATTTACTCATTATCGCCTTTTGACAGC    2220
TGTGCTGTAACACAAGTAGATGCCTGAACT    2250
TGAATTAATCCACACATCAGTAATGTATTC    2280
TATCTCTCTTTACATTTTGGTCTCTATACT    2310
ACATTATTAATGGGTTTTGTGTACTGTAAA    2340
GAATTTAGCTGTATCAAACTAGTGCATGAA    2370
TAGATTCTCTCCTGATTATTTATCACATAG    2400
CCCCTTAGCCAGTTGTATATTATTCTTGTG    2430
GTTTGTGACCCAATTAAGTCCTACTTTACA    2460
TATGCTTTAAGAATCGATGGGGGATGCTTC    2490
ATGTGAACGTGGGAGTTCAGCTGCTTCTCT    2520
TGCCTAAGTATTCCTTTCCTGATCACTATG    2550
CATTTTAAAGTTAAACATTTTTAAGTATTT    2580
CAGATGCTTTAGAGATTTTTTTTCCATG     2610
ACTGCATTTTACTGTACAGATTGCTGCTTC    2640
TGCTATATTTGTGATATAGGAATTAAGAGG    2670
ATACACGTTTGTTTCTTCGTGCCTGTTT     2700
TATGTGCACACATTAGGCATTGAGACTTCA    2730
AGCTTTTCTTTTTTTGTCCACGTATCTTTG    2760
GGTCTTTGATAAAGAAAAGAATCCCTGTTC    2790
ATTGTAAGCACTTTTACGGGGCGGGTGGGG    2820
AGGGGTGCTCTGCTGGTCTTCAATTACCAA    2850
GAATTCTCCAAAACAATTTTCTGCAGGATG    2880
ATTGTACAGAATCATTGCTTATGACATGAT    2910
CGCTTTCTACACTGTATTACATAAATAAAT    2940
TAAATAAAATAACCCCGGGCAAGACTTTTC    2970
TTTGAAGGATGACTACAGACATTAAATAAT    3000
```

-continued

```
CGAAGTAATTTTGGGTGGGGAGAAGAGGCA    3030
GATTCAATTTTCTTTAACCAGTCTGAAGTT    3060
TCATTTATGATACAAAAGAAGATGAAAATG    3090
GAAGTGGCAATATAAGGGGATGAGGAAGGC    3120
ATGCCTGGACAAACCCTTCTTTTAAGATGT    3150
GTCTTCAATTTGTATAAAATGGTGTTTTCA    3180
TGTAAATAAATACATTCTTGGAGGAGC-poly(A)tail
``` and functional equivalents thereof.

2. A deoxyribonucleic acid according to claim 1 of the sequence:

```
ATGCTGCCCGGTTTGGCACTGCTCCTGCTG      30
 M  L  P  G  L  A  L  L  L  L

GCCGCCTGGACGGCTCGGGCGCTGGAGGTA      60
 A  A  W  T  A  R  A  L  E  V

CCCACTGATGGTAATGCTGGCCTGCTGGCT      90
 P  T  D  G  N  A  G  L  L  A

GAACCCCAGATTGCCATGTTCTGTGGCAGA     120
 E  P  Q  I  A  M  F  C  G  R

CTGAACATGCACATGAATGTCCAGAATGGG     150
 L  N  M  H  M  N  V  Q  N  G

AAGTGGGATTCAGATCCATCAGGGACCAAA     180
 K  W  D  S  D  P  S  G  T  K

ACCTGCATTGATACCAAGGAAGGCATCCTG     210
 T  C  I  D  T  K  E  G  I  L

CAGTATTGCCAAGAAGTCTACCCTGAACTG     240
 Q  Y  C  Q  E  V  Y  P  E  L

CAGATCACCAATGTGGTAGAAGCCAACCAA     270
 Q  I  T  N  V  V  E  A  N  Q

CCAGTGACCATCCAGAACTGGTGCAAGCGG     300
 P  V  T  I  Q  N  W  C  K  R

GGCCGCAAGCAGTGCAAGACCCATCCCCAC     330
 G  R  K  Q  C  K  T  H  P  H

TTTGTGATTCCCTACCGCTGCTTAGTTGGT     360
 F  V  I  P  Y  R  C  L  V  G

GAGTTTGTAAGTGATGCCCTTCTCGTTCCT     390
 E  F  V  S  D  A  L  L  V  P

GACAAGTGCAAATTCTTACACCAGGAGAGG     420
 D  K  C  K  F  L  H  Q  E  R

ATGGATGTTTGCGAAACTCATCTTCACTGG     450
 M  D  V  C  E  T  H  L  H  W

CACACCGTCGCCAAAGAGACATGCAGTGAG     480
 H  T  V  A  K  E  T  C  S  E

AAGAGTACCAACTTGCATGACTACGGCATG     510
 K  S  T  N  L  H  D  Y  G  M

TTGCTGCCCTGCGGAATTGACAAGTTCCGA     540
 L  L  P  C  G  I  D  K  F  R

GGGGTAGAGTTTGTGTGTTGCCCACTGGCT     570
 G  V  E  F  V  C  C  P  L  A

GAAGAAAGTGACAATGTGGATTCTGCTGAT     600
 E  E  S  D  N  V  D  S  A  D

GCGGAGGAGGATGACTCGGATGTCTGGTGG     630
 A  E  E  D  D  S  D  V  W  W
```

-continued

```
GGCGGAGCAGACACAGACTATGCAGATGGG     660
 G  G  A  D  T  D  Y  A  D  G

AGTGAAGACAAAGTAGTAGAAGTAGCAGAG     690
 S  E  D  K  V  V  E  V  A  E

GAGGAAGAAGTGGCTGAGGTGGAAGAAGAA     720
 E  E  E  V  A  E  V  E  E  E

GAAGCCGATGATGACGAGGACGATGAGGAT     750
 E  A  D  D  D  E  D  D  E  D

GGTGATGAGGTAGAGGAAGAGGCTGAGGAA     780
 G  D  E  V  E  E  E  A  E  E

CCCTACGAAGAAGCCACAGAGAGAACCACC     810
 P  Y  E  E  A  T  E  R  T  T

AGCATTGCCACCACCACCACCACCACCACA     840
 S  I  A  T  T  T  T  T  T  T

GAGTCTGTGGAAGAGGTGGTTCGAGTTCCT     870
 E  S  V  E  E  V  V  R  V  P

ACAACAGCAGCCAGTACCCCTGATGCCGTT     900
 T  T  A  A  S  T  P  D  A  V

GACAAGTATCTCGAGACACCTGGGGATGAG    930
 D  K  Y  L  E  T  P  G  D  E

AATGAACATGCCCATTTCCAGAAAGCCAAA     960
 N  E  H  A  H  F  Q  K  A  K

GAGAGGCTTGAGGCCAAGCACCGAGAGAGA    990
 E  R  L  E  A  K  H  R  E  R

ATGTCCCAGGTCATGAGAGAATGGGAAGAG   1020
 M  S  Q  V  M  R  E  W  E  E

GCAGAACGTCAAGCAAAGAACTTGCCTAAA   1050
 A  E  R  Q  A  K  N  L  P  K

GCTGATAAGAAGGCAGTTATCCAGCATTTC   1080
 A  D  K  K  A  V  I  Q  H  F

CAGGAGAAAGTGGAATCTTTGGAACAGGAA   1110
 Q  E  K  V  E  S  L  E  Q  E

GCAGCCAACGAGAGACAGCAGCTGGTGGAG   1140
 A  A  N  E  R  Q  Q  L  V  E

ACACACATGGCCAGAGTGGAAGCCATGCTC   1170
 T  H  M  A  R  V  E  A  M  L

AATGACCGCCGCCGCCTGGCCCTGGAGAAC   1200
 N  D  R  R  R  L  A  L  E  N

TACATCACCGCTCTGCAGGCTGTTCCTCCT   1230
 Y  I  T  A  L  Q  A  V  P  P

CGGCCTCGTCACGTGTTCAATATGCTAAAG   1260
 R  P  R  H  V  F  N  M  L  K

AAGTATGTCCGCGCAGAACAGAAGGACAGA   1290
 K  Y  V  R  A  E  Q  K  D  R

CAGCACACCCTAAAGCATTTCGAGCATGTG   1320
 Q  H  T  L  K  H  F  E  H  V

CGCATGGTGGATCCCAAGAAAGCCGCTCAG   1350
 R  M  V  D  P  K  K  A  A  Q

ATCCGGTCCCAGGTTATGACACACCTCCGT   1380
 I  R  S  Q  V  M  T  H  L  R

GTGATTTATGAGCGCATGAATCAGTCTCTC   1410
 V  I  Y  E  R  M  N  Q  S  L

TCCCTGCTCTACAACGTGCCTGCAGTGGCC   1440
 S  L  L  Y  N  V  P  A  V  A

GAGGAGATTCAGGATGAAGTTGATGAGCTG   1470
 E  E  I  Q  D  E  V  D  E  L

CTTCAGAAAGAGCAAAACTATTCAGATGAC   1500
 L  Q  K  E  Q  N  Y  S  D  D

GTCTTGGCCAACATGATTAGTGAACCAAGG   1530
 V  L  A  N  M  I  S  E  P  R

ATCAGTTACGGAAACGATGCTCTCATGCCA   1560
 I  S  Y  G  N  D  A  L  M  P

TCTTTGACCGAAACGAAAACCACCGTGGAG   1590
 S  L  T  E  T  K  T  T  V  E

CTCCTTCCCGTGAATGGAGAGTTCAGCCTG   1620
 L  L  P  V  N  G  E  F  S  L

GACGATCTCCAGCCGTGGCATTCTTTTGGG   1650
 D  D  L  Q  P  W  H  S  F  G

GCTGACTCTGTGCCAGCCAACACAGAAAAC   1680
 A  D  S  V  P  A  N  T  E  N

GAAGTTGAGCCTGTTGATGCCCGCCCTGCT   1710
 E  V  E  P  V  D  A  R  P  A

GCCGACCGAGGACTGACCACTCGACCAGGT   1740
 A  D  R  G  L  T  T  R  P  G

TCTGGGTTGACAAATATCAAGACGGAGGAG   1770
 S  G  L  T  N  I  K  T  E  E

ATCTCTGAAGTGAAGATGGATGCAGAATTC   1800
 I  S  E  V  K  M  D  A  E  F

CGACATGACTCAGGATATGAAGTTCATCAT   1830
 R  H  D  S  G  Y  E  V  H  H

CAAAAATTGGTGTTCTTTGCAGAAGATGTG   1860
 Q  K  L  V  F  F  A  E  D  V

GGTTCAAACAAAGGTGCAATCATTGGACTC   1890
 G  S  N  K  G  A  I  I  G  L

ATGGTGGGCGGTGTTGTCATAGCGACAGTG   1920
 M  V  G  G  V  V  I  A  T  V

ATCGTCATCACCTTGGTGATGCTGAAGAAG   1950
 I  V  I  T  L  V  M  L  K  K

AAACAGTACACATCCATTCATCATGGTGTG   1980
 K  Q  Y  T  S  I  H  H  G  V

GTGGAGGTTGACGCCGCTGTCACCCCAGAG   2010
 V  E  V  D  A  A  V  T  P  E

GAGCGCCACCTGTCCAAGATGCAGCAGAAC   2040
 E  R  H  L  S  K  M  Q  Q  N

GGCTACGAAAATCCAACCTACAAGTTCTTT   2070
 G  Y  E  N  P  T  Y  K  F  F

GAGCAGATGCAGAACTAGA
 E  Q  M  Q  N  *
``` and functional equivalents thereof.

3. A deoxyribonucleic acid fragment according to claim 1 of the sequence:

```
GGGGTAGAGTTTGTGTGTTGCCCACTGGCT      570
 G  V  E  F  V  C  C  P  L  A

GAAGAAAGTGACAATGTGGATTCTGCTGAT     600
 E  E  S  D  N  V  D  S  A  D

GCGGAGGAGGATGACTCGGATGTCTGGTGG     630
 A  E  E  D  D  S  D  V  W  W

GGCGGAGCAGACACAGACTATGCAGATGGG     660
 G  G  A  D  T  D  Y  A  D  G
```

```
AGT GAA GAC AAA GT AGT AGA AGT AGC AGAG      690
 S   E   D   K   V   V   E   V   A   E

GAG GAA GAA GT GGCT GAG GT GGA AGA AGAA      720
 E   E   E   V   A   E   V   E   E   E

GAA GCC GAT GAT GAC GAG GAC GAT GAG GAT      750
 E   A   D   D   D   E   D   D   E   D

GGT GAT GAG GT AGA GGA AGA GGCT GAG GAA      780
 G   D   E   V   E   E   E   A   E   E
```

```
CCCT ACG AAG AAG CCA CAG AGA GAA CCACC       810
 P   Y   E   E   A   T   E   R   T   T

AGC ATT GCC ACC ACC ACC ACC ACC ACC ACA      840
 S   I   A   T   T   T   T   T   T

GAG TCT GT GGA AGA GGT GGT TCG AGT TCCT      870
 E   S   V   E   E   V   V   R   V   P

ACA ACA GCA GCC AGT ACC CCT GAT GCC GTT      900
 T   T   A   A   S   T   P   D   A   V
``` and functional equivalents thereof.

* * * * *